United States Patent
Querfurth

(10) Patent No.: US 7,122,007 B2
(45) Date of Patent: Oct. 17, 2006

(54) METHODS OF AND SYSTEMS AND DEVICES FOR ASSESSING INTRACRANIAL PRESSURE NON-INVASIVELY

(75) Inventor: Henry W. Querfurth, Wellesley, MA (US)

(73) Assignee: Caritas St. Elizabeth Medical Center of Boston, Inc., Cambridge, MA (US)

( * ) Notice: Subject to any disclaimer, the term of this patent is extended or adjusted under 35 U.S.C. 154(b) by 450 days.

(21) Appl. No.: 10/436,548

(22) Filed: May 12, 2003

(65) Prior Publication Data

US 2004/0230124 A1  Nov. 18, 2004

(51) Int. Cl.
 A61B 5/02 (2006.01)
 A61B 5/00 (2006.01)

(52) U.S. Cl. .............. 600/485; 600/561; 600/481

(58) Field of Classification Search .......... 600/481, 600/485, 486, 561, 483
See application file for complete search history.

(56) References Cited

U.S. PATENT DOCUMENTS

| | | | |
|---|---|---|---|
| 3,835,836 A | 9/1974 | Kanter et al. | 128/2 T |
| 3,903,871 A | 9/1975 | Chisum et al. | 128/2 T |
| 3,929,124 A | 12/1975 | Yablonski et al. | 128/2 T |
| 4,907,595 A | 3/1990 | Strauss | 128/661.06 |
| 4,922,913 A | 5/1990 | Waters, Jr. et al. | 128/645 |
| 5,291,899 A | 3/1994 | Watanabe et al. | 128/746 |
| 5,830,139 A * | 11/1998 | Abreu | 600/405 |
| 6,027,454 A | 2/2000 | Löw | 600/489 |
| 6,086,533 A | 7/2000 | Madsen et al. | 600/438 |
| 6,120,460 A * | 9/2000 | Abreu | 600/558 |
| 6,123,668 A * | 9/2000 | Abreu | 600/405 |
| 6,129,682 A * | 10/2000 | Borchert et al. | 600/561 |
| 6,213,943 B1 * | 4/2001 | Abreu | 600/405 |
| 6,312,393 B1 * | 11/2001 | Abreu | 600/558 |
| 6,347,242 B1 * | 2/2002 | Friedlander | 600/431 |
| 6,390,989 B1 * | 5/2002 | Denninghoff | 600/561 |
| 6,423,001 B1 * | 7/2002 | Abreu | 600/405 |
| 6,544,193 B1 * | 4/2003 | Abreu | 600/558 |
| 6,875,176 B1 * | 4/2005 | Mourad et al. | 600/442 |

OTHER PUBLICATIONS

H.W. Querfurth, et al., "Flow Velocity and Pulsatility of the Ocular Circulation in Chronic Intracranial Hypertension", Acta Neurologica Scandinavica 2002: 105: pp. 431-440.

M. Motschmann, et al., "Ophthalmodynamometrie," Ophthalomologe 2000.97: pp. 860-862, Springer-Verlag 2000.

M. Salman, "Non-invasive Measurement of Intracranial Pressure" The Lancet, vol. 351, pp. 523-525, Feb. 14, 1998.

R. Firsching, et al., "Venous Ophthalmodynamometry: A Noninvasive Method for Assessment of Intracranial Pressure." J. Neurosureg, vol. 93, pp. 33-36, Jul. 2000.

M. Motschmann, et al., "Ophthalmodynamometry: A Reliable Method for Measuring Intracranial Pressure." Strabismus- 2001, vol. 9, No. 1 pp. 13-16.

* cited by examiner

Primary Examiner—Robert L. Nasser
Assistant Examiner—Navin Natnithithadha
(74) Attorney, Agent, or Firm—Edwards Angell Palmer & Dodge LLP; David G. Conlin; Linda M. Buckley

(57) ABSTRACT

A non-invasive method and system for assessing intraocular pressure (ICP) is disclosed. The method comprises the steps of measuring venous outflow pressure (VOP) using a venous ophthalmodynamometer device (vODM); measuring ophthalmic r central retinal arterial blood flow using color Doppler imaging device; and then estimating ICP using venous outflow data from the vODM and pulsatility and/or resistivity relationships derived from the Doppler imaging data. Further disclosed is a novel vODM for measuring VOP in low flow veins.

20 Claims, 5 Drawing Sheets

METHODS OF AND SYSTEMS AND DEVICES FOR ASSESSING INTRACRANIAL PRESSURE NON-INVASIVELY

FIELD OF THE INVENTION

The present invention relates to methods of and systems and devices for predicting intracranial pressure. More specifically, the present invention relates to methods, systems and devices for predicting absolute intracranial pressure and changes in intracranial pressure non-invasively, by measuring retinal venous pressure and arterial pulsatility.

BACKGROUND OF THE INVENTION

Continuous measurement and monitoring of intracranial pressure (ICP) for instantaneous (absolute) pressures as well as changes in pressure, especially among patients with, e.g., head injury, stroke edema, and acute intracranial hemorrhage, provides necessary, sometimes vital information on which medical and surgical treatment can be based. Heretofore and currently, invasive techniques have been used despite the many shortcomings of such practice. Continuous ICP measuring devices to manage intracranial hypertension (ICH) require invasive surgical boring through the skull to emplace them. Alternatively, another standard option for serial measurement of ICP is to repeat puncture of the lumbar dura, i.e., spinal tap, to measure the cerebrospinal fluid (CSF) pressure. For our purposes, CSF pressure is used interchangeably with ICP since both are essentially equivalent. Such procedures carry the risk of hemorrhage, malfunction, herniation and/or infection and, furthermore, are quite expensive. Representative examples of invasive ICP measuring devices and monitors include subarachnoid bolts, counterpressure epidural and subdural devices, e.g., Ladd or Camino fiberoptic monitors and Gaeltec sensors, intraparenchymal microsensors, and intra-ventricular catheters coupled to an external fluid pressure transducer.

Other approaches have been proposed to provide means to measure ICP non-invasively. Proposed techniques include measurement of tympanic membrane displacement in the ear, ultrasonic detection of cranial pulsations, and transcranial Doppler (TCD) ultrasonography of the middle cerebral artery. However, practical limitations prevent their use.

For example, the tympanic membrane displacement method is based on acoustic stapedial reflex that, in theory, can measure intracranial pressure indirectly by measuring displacement of the eardrum since ICP is transmitted from the CSF to the perilymphatic fluid of the scala tympana in the labyrinth. Drawbacks to this method include the indirect nature of measurement and the necessity of having a patent, unobstructed cochlear aqueduct.

TCD ultrasonography provides a real-time spectral waveform of blood flow velocity in intracranial vessels. However, with many head injury patients, flow velocities in unilateral intracranial vessels may either increase or decrease due to vasospasms, loss of normal cerebrovascular auto-regulation or other reasons. Furthermore, other physiologic variables, e.g., cardiac output, pulse rate, hematocrit, positive end expiratory pressure (if ventilated), and carbon dioxide tension can alter TCD parameters. Accordingly, TCD ultrasonography cannot predict absolute ICP from instantaneous readings. As a result, one can only infer trends. Finally, insonation of intracranial vessels requires technical training in order to deal with the complexity and anatomic variability of the cerebral vasculature.

Alternatively, use of extracranial ocular blood vessels to measure or assess ICP non-invasively as been suggested. Those skilled in the art recognize that increases in ICP affect the valveless venous system that drains the orbits. Indeed, venous distension due to increased resistance (or back pressure) to drainage is an obvious sign in late papilledema. Thus, those skilled in the art have sought means for assessing or measuring ICP using measurements of venous pressure in optic nerves.

Baurmann is believed to have been the first to suggest assessing ICP by measuring the pressure within the central retinal vein (CRV). The CRV caries venous blood away from the retina and toward the cavernous sinus of the brain. However, Baurmann's theory and findings, which appeared in the mid 1920's, have had to wait for technological advances for verification. Baurmann knew that CSF surrounds the optic nerve and therefore the optic nerve is subjected to ambient ICP. The extraocular segment of the CRV courses through the optic nerve, where the resistance to flow is dependent on the prevailing CSF pressure. This pressure is transmitted onto the thin wall of the vein through the nerve tissue. Further upstream, intraocular venous drainage from the retina and over the optic nerve head must overcome this resistance to outflow at its point of exit into the optic nerve. When ICP is excessive, the extraocular CRV and axons, coursing within the optic nerve, are tamponaded. The result is a rapid rise in intraluminal venous pressure and engorgement of the CRV at the optic nerve head (as well as papilledema if chronic). Distension and pulsation of the CRV branches can be visualized at this location by standard ophthalmoscopy, wherein the pressure gradient across the vein wall is the difference between intraocular pressure (IOP) and the intraluminal venous blood pressure.

The CRV pressure is usually equal to or higher than the ICP in the extraocular segment and, moreover, equal to or slightly higher than the IOP in the intraocular segment, otherwise no flow would occur between the compartments. When approximately equal to the IOP, the vein at the nerve head is found to pulsate; however, in other normal individuals it is not found to pulsate because the resting pressure is slightly higher than the IOP. According to Walsh, the major mechanism of the pulsations is partial collapse from variations in the IOP induced by arterial flow patterns on the extravascular vitreous.

If the IOP is now increased above the venous pressure, the vein will easily collapse. The manipulated IOP at the moment of venous collapse is defines as the venous outflow pressure (VOP). The VOP is, essentially, equal to the central retinal vein (CRV) pressure within the extraocular, intraoptic nerve segment. On the other hand, as ICP increases above about 20 cm $H_2O$ (intracranial hypertension), retinal vein pulsations, if present at rest, will first disappear. With further increases in ICP, the veins begin to engorge and become increasingly more difficult to collapse, requiring higher levels of IOP production to find the new VOP. The appearance of the CRV, therefore, reflects whichever compartment—the IOP or ICP—is higher.

Although the VOP is always found somewhat higher than the actual ICP, there is a direct correspondence between them. From the above discussion, the means to estimate actual ICP from graded increases in IOP is provided.

Others have also proposed noninvasive method for assessing ICP by venous ophthalmodynamometry (ODM). ODM refers to use of a calibrated compression-biased spring gauge device, or, alternatively, a vacuum cup, to manipulate IOP in ophthalmologic practice. ODM was pioneered by Bailliart, who, in 1917, observed that retinal arterial blood vessels, i.e., the central retinal artery, begin to pulsate at the point when IOP exceeds the diastolic arterial pressure and pulsations disappear when systolic pressures are reached.

Bailliart applied a hand-held device onto the anaesthetized lateral sclera of a patient and watched for the arteries to pulsate or cease pulsating. The device comprised a small pressure plate disposed at the end of a spring-loaded plunger. The spring was coupled to a dial gauge, which was calibrated to correlate applied pressure (in grams) to displacement of the plunger and compression of the spring. After the user applied the pressure plate/plunger to the patient's orbit (sclera), pressure was incrementally increased. This caused the spring to compress in a manner linear with the rise in IOP. The user continued to apply pressure until he or she observed pulsations come and go and finally loss of arterial color.

Using a nomograph and a baseline IOP readings taken using a tonometer while the patient was resting, one can convert the pressure on the dial gauge at the instant of arterial wall changes as seen through an ophthalmoscope, to the actual induced IOP. Although sophisticated enough to measure pressure in the arterial range, which is not correlated with ICP, the Bailliart device is not sensitive enough to determine the anticipated direct relationship between ICP and lower retinal pressures.

The inventor incorporates by reference herein an article entitled "Flow velocity and pulsatility of the ocular circulation in chronic intracranial hypertension," which appeared in Acta Neurologica Scandinavica 2002: Volume 105, pps. 431–440, that he co-authored. In the article, the authors reported that, "orbital arterial velocities and pulsatility/resistance indices are significantly affected by ICP changes in chronic raised ICH." However, that being said, the authors further observed and reported a non-linear, bi-modal relationship between pulsatility/resistance indices, e.g., Gosling's Pulsatility Index (GPI), and ICP for both flow measurements for the central retinal artery (CRA) and the ophthalmic artery (OA). In summary, the authors concluded that, the biphasic relationship is a function of both the CSF, i.e., whether mild-to-moderate or severe-to-extreme, and compensatory regional changes in arterial flow pattern. As a result, the Ocular Color-Doppler sonography could not be used to predict ICP in chronic raised ICP.

More recently, Firsching, et al. reported a correlation between VOP and ICP using an ODM device fashioned by themselves for non-invasive assessment of IOP. First, Firsching, et al. established a baseline IOP using a tonometer. Subsequently, Firsching, et al. attached a suction cup to a patient's lateral eye bulb and applied negative pressure, i.e., a vacuum, to the eye bulb, to increase IOP. As the pressure was applied, Firsching, et al. observed the CRV to the point of collapse using indirect funduscopy. At the instance of vein collapse, the ODM measurement and ICP were recorded simultaneously. The ODM measurement, further, was converted to IOP, which was equated to VOP. Firsching, et al. then plotted VOP versus ICP and through regression analysis derived an empirical, linear formula for assessing ICP.

The assessment technique developed by Firsching, et al., however, did not address or take into account the contribution to venous outflow pressure made by retinal arterial hemodynamic parameters, e.g., perfusion (flow volume), velocity, pressure, pulsatility, and resistance to flow. Furthermore, indirect funduscopy requires considerably more technical experience to operate than direct ophthalmoscopy as used herein. Moreover, application of a suction cup-based ODM is also more technically demanding, requires a more cumbersome apparatus, and is more uncomfortable to the patient than methods described herein.

SUMMARY OF THE INVENTION

In a first embodiment, the present invention provides non-invasive method of assessing at least one of an absolute and a change in intracranial pressure (ICP), the method comprising the steps:
  measuring venous outflow pressure (VOP);
  measuring ophthalmic or central retinal arterial blood flow velocity; and
  determining intracranial pressure (ICP) using venous outflow pressure (VOP) data and a characteristic of ophthalmic artery from the ophthalmic or central retinal arterial velocity data.

Preferably, VOP is measured using a venous ophthalmodynamometer that comprises a displacement transducer in combination with a frequency analyzer and arterial blood flow velocity is measured by color Doppler imaging. More preferably, pressure is applied to the anesthetized orbit of a patient using the pressure plate of the displacement transducer, which induces a current that is transmitted as an analog signal to the frequency analyzer. The frequency analyzer receives the analog data, which it stores, manipulates, and displays as VOP.

Furthermore, preferably, color Doppler imaging provides a real time ultrasonic, signal of arterial blood flow and direction in a discrete arterial vessel in the patient's orbit. These data are used to calculate pulsatility and resistance indices, which, in turn, can be used in conjunction with the VOP to refine the estimate of ICP.

In a second embodiment, the present invention provides a non-invasive system for assessing at least one of an absolute and a change in intracranial pressure (ICP), the system comprising:
  a venous outflow pressure (VOP) measuring device;
  an ophthalmic or central retinal arterial blood flow velocity measuring device; and
  a device for estimating intracranial pressure (ICP) using venous outflow pressure (VOP) data and a characteristic of the ophthalmic or central retinal artery from the ophthalmic or central retinal arterial flow velocity data.

Preferably, the system uses a venous ophthalmodynamometer, comprising a displacement transducer in combination with a frequency analyzer, to measure VOP. Arterial blood flow velocity is measured by color Doppler imaging. More preferably, the pressure plate of the displacement transducer applies graded pressure to the lateral sclera orbit of a patient, which induces a current in an induction device commensurate with the magnitude of displacement. The induced current provides an analog signal that is transmitted to the frequency analyzer. The frequency analyzer receives the analog data; digitizes the data; and further stores, manipulates, and displays the data as VOP.

Furthermore, preferably, a color Doppler imaging (CDI) device comprising a Doppler probe and a spectral analyzer, is used to provide a real time ultrasonic, signal of arterial blood flow in a discrete arterial vessel in the patient's orbit. These data are used to calculate pulsatility and resistance indices, which, in turn, can be used in conjunction with VOP data to refine the estimate of ICP.

BRIEF DESCRIPTION OF THE DRAWINGS

For a fuller understanding of the nature and desired objects of the present invention, reference is made to the following detailed description taken in conjunction with the accompanying figures wherein like reference characters denote corresponding parts throughout the several views and wherein.

DETAILED DESCRIPTION OF THE INVENTION

Figure 1:
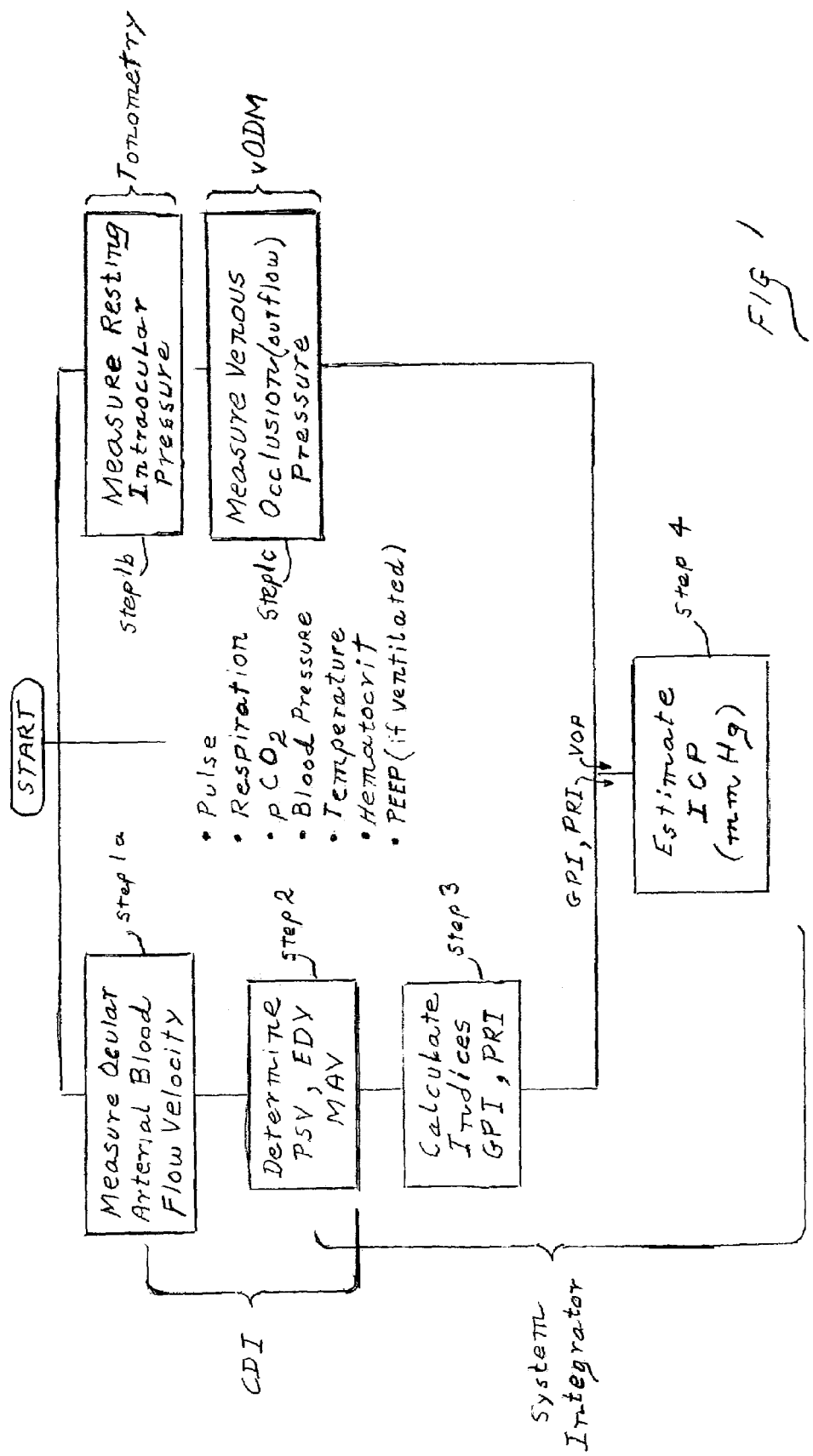
FIG. 1 shows a flow diagram of an illustrative embodiment of a method of assessing ICP in accordance with the present invention.

In a first embodiment, the present invention comprises a method of assessing intracranial pressure (ICP), which is shown in a flow diagram in FIG. 1. Preferably, the method collects data on central retinal arterial (CRA) and/or ophthalmic arterial (OA) flow velocities STEP 1a, establishes a baseline, resting intraocular pressure (IOP) STEP 1b, and collects data on retinal vein occlusion, or outflow, pressure (VOP) STEP 1c. More preferably, the embodied method collects data on retinal and ophthalmic arterial flow velocities STEP 1a using a color Doppler imaging (CDI) device 22 (See FIG. 2) and collects data on venous ocular pressure (VOP) STEP 1c using a portable venous ophthalmodynamometer (vODM) 30, which devices are described in greater detail below.

Color Doppler imaging (CDI) is known to the art and the mechanics of a CDI device 22 will not be described in great detail herein except as they relate to the present invention. The inventor used a bulky Siemens Q 2000 or Elegra unit 22 having a 7.5 MHz, pulsed-wave, linear transducer, i.e., Doppler probe 21, which unit or like units is common to most hospitals, to measure arterial blood flow velocities of supine patients. However, the invention should not be construed as being so limited as portable transcranial Doppler (TCD) systems are commercially available, e.g., the Neuroflow™ TCD system manufactured by Neuroguard of Fremont, Calif., that one skilled in the art could adapt for use with the system 20 and method of the present invention.

The CDI device 22 is in communication with a linear transducer (or probe) 21 via an inlet/outlet (I/O) port 23. Preferably, the Doppler probe is in the form of a linear transducer 21 is positioned manually near one of the orbits 25 of a patient. More preferably, the Doppler probe 21 can be applied to the closed eyelid 26 of a supine patient. In one aspect of the present invention, ultrasound levels in the about 50 to about 100 MW/cm$^2$ range and more preferably at a level of about 71 MW/cm$^2$ can be used at about 50 percent power. In a second aspect of the present invention, the CDI device 22 is multimodal, and one mode (B-mode) of the device 22 can provide an image of an organ; another mode (C-mode) of the device 22 can provide a visualization of the anterograde arterial flow; and another mode (D-mode) of the device 22 can measure arterial flow velocities. Those skilled in the art can adjust the Doppler angle as desired to achieve maximal velocity signal, however.

More preferably, the Doppler probe 21 and CDI device 22 are structured and arranged to send a visual image, e.g., two-dimensional, black and white image, of the optic nerve head of the eye in the orbit 25 to the CDI device 22, e.g., using the B-mode; to send a real time, spatially visualized color Doppler image of anterograde arterial flow in the B-mode image, e.g., using the C-mode; and to send a pulsed-wave, ultrasound signal of the arterial blood flow velocity and direction, e.g., using the D-mode. The D-mode signal can be digitized and used to calculate Doppler frequency shifts that, in turn, can be used to calculate arterial systolic and diastolic blood flow velocity. This preferred ultrasonography provides a real-time spectral waveform measurement of blood flow in ocular arteries.

In another aspect of the present invention, the CDI device 22 includes software and/or hardware to display the image from the linear transducer 21 on a display (not shown), e.g., as a two-dimensional orbital B-scan. An input/output (I/O) device(s) (not shown), e.g., a mouse, further, can be in communication with the CDI device 22 to enable the user to move a cursor on the screen displaying the two-dimension orbital B-scan to pinpoint a region or point of interest from which arterial blood flow measurements can be made. The central retinal artery (CRA) and central retinal vein (CRV) typically are located for Doppler measurement purposes approximately 2 mm behind the optic nerve head and sounding depth for the CRA is between about 25 and about 30 mm. Alternatively or additionally, the ophthalmic artery (OA) (nasal side) is located about 15 mm behind the eye nasal to the optic nerve and sounding depths are between about 40 and about 50 mm. Preferably, the cursor is disposed at one or more of these locations.

In a D-mode, the Doppler probe 21 sends continuous ultrasound analog signals of Doppler frequency shifts in the blood coursing through the CRA or OA, which produce spectral, flow measurement data. Although the CRA and OA are discussed herein as the best mode, the invention is not to be construed as being limited to measurements made in just those two arteries. For example, the posterior ciliary arteries also can be used for purposes of blood flow measurement. Software and/or hardware in the CDI device 22 can display these flow measurement data as velocity versus time graphs.

In a second step, the blood flow measurements from the CDI device 22 can be used to extract arterial blood flow parameters in STEP 2. Preferably, software and/or hardware, e.g., a spectral analyzer (not shown), installed in or in communication with the CDI device 22, can digitize the ultrasound arterial blood flow signal, e.g., ultrasonic D-mode, signal and determine therefrom peak systolic velocity (PSV), end diastolic velocity (EDV), and mean arterial velocity (MAV) of the blood flow for at least one of the CRA and the OA. Generally, blood flow measurements from the CRA provide a better predictor of ICP than OA measurements; however, OA measurements provide acceptable data. These data can, further, be output to a system integrator 29.

In STEP 3, the system integrator 29 can use these data to calculate at least one of Gosling's Pulsatility Index (GPI), which is defined by the equation:

$$GPI=(PSV-EDV)/MAV$$

and Pourcelot's Resistive Index (PRI) STEP 3, which is defined by the equation:

$$PRI=(PSV-EDV)/PSV.$$

These indices provide normalized measures of the pulsatility/resistivity of blood flow in the CRA, which the inventor has discovered is valuable in assessing ICP non-invasively.

The embodied method further comprises the step of measuring venous outflow pressure (VOP) STEP 1c. Preferably, VOP is measured simultaneously or immediately after the arterial blood flow velocity is measured STEP 1a. More preferably, VOP can be measured using a direct ophthalmoscope (not shown) of a type that is well known to the art in combination with a portable venous ophthalmodynamometer (vODM) 30 of a type and in a manner described in greater detail below. Succinctly, pressure is applied to the lateral sclera of a patient's orbit 25 until the patient's CRV or other retinal vein occludes, or collapses, the pressure at which corresponds to the VOP.

Preferably, as pressure is applied to the patient's orbit 25 to the point of collapse, the CRV is directly monitored visually, e.g., using a hand-held ophthalmoscope. In contrast to indirect funduscopy, which is the observation means employed by Firsching, et al., use of an ophthalmoscope in the embodied method is simpler, requiring less training to master, and provides direct, as opposed to indirect, observation of the orbit 25.

More preferably, pressure is applied to the patient's orbit 25 to the point of collapse using a displacement transducer 32 and the CRV is monitored visually using an ophthalmoscope. The displacement transducer 32 and the ophthalmoscope are hand held devices that can be operated by a single user or multiple users working in tandem. At the point or collapse of the CRV, pressure is no longer applied to the orbit 25 and the force, typically measured in grams (g), at the point of occlusion can be digitally recorded. To facilitate measurements, the vODM 30 can further comprise a foot pedal 39, which the user can activate, e.g., manually or with his or her foot, when he or she observes occlusion of the CRV, thereby automatically freezing and storing the VOP at the point of collapse.

In a preferred embodiment, use of a vODM 30 in combination with an ophthalmoscope to measure VOP includes first anesthetizing the orbit 25, e.g., using topical proparacaine HCl 0.5% dilated with Tropicamide (Midriacyl, 1%), and dilating the patient's pupil pharmacologically so that application of a pressure plate 38 of a displacement transducer 32 does not produce an involuntary reflex, e.g., blinking, of the orbit 25. Once the orbit 25 is anesthetized and the pupil dilated, a sanitized pressure plate 38, which is structured and arranged at the distal end of the displacement transducer 32, can be applied to a patient's orbit 25 and pressure can be applied to a patient's orbit 25 incrementally. As pressure is applied to the orbit 25, the user can visually monitor one of the retinal veins through the unoccluded cornea and pupil, well out of the way of the pressure plate 38. Application of force continues incrementally to the point of collapse, or occlusion, which is observable with the ophthalmoscope. Activation of the foot pedal 39 at the point of occlusion facilitates recording the instantaneous pressure at collapse. To provide an average VOP, this procedure can be repeated several times.

Figure 6:
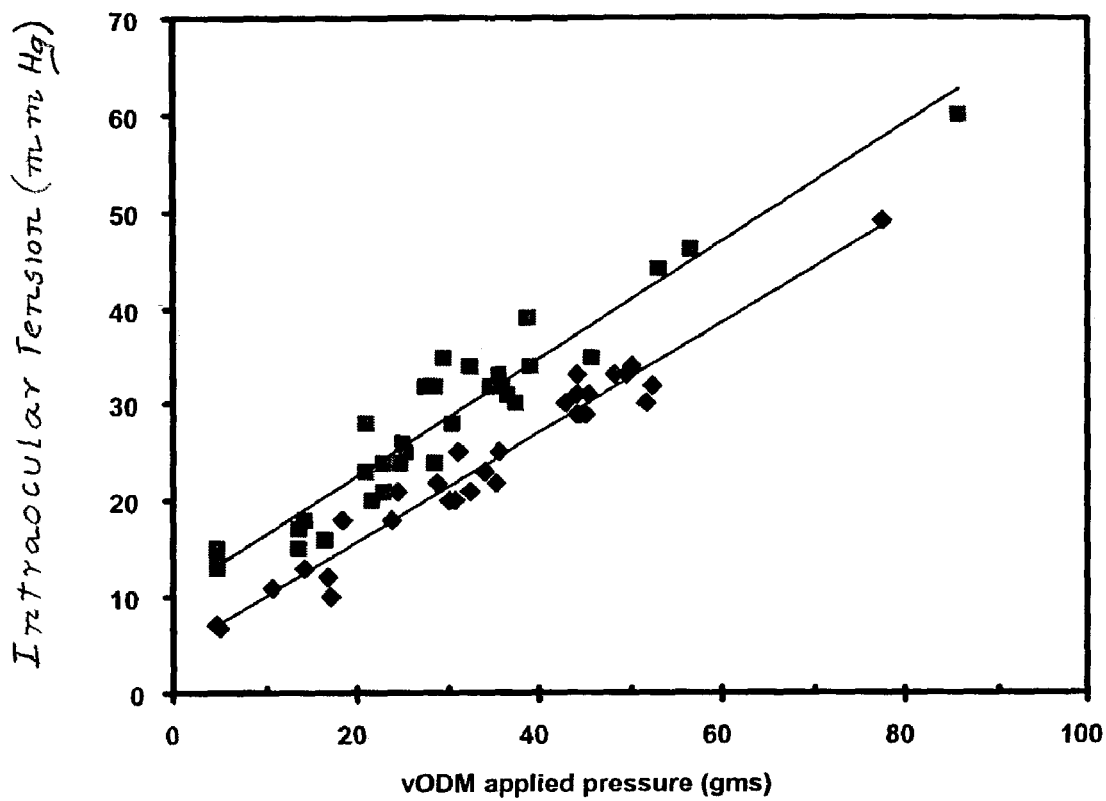
FIG. 6 shows an illustrative conversion chart showing the relationship between applied ocular pressure (using a vODM transducer) and intraocular pressure (using a tonometer) to adjust VOP measurements from baseline, resting IOP.

VOP (in mm Hg) can then be calculated as a function of the applied force (in grams) at the point of collapse and resting IOP, which can be measured, e.g., using a tonometer, contemporaneously with but prior to VOP testing while the patient is in a supine or "resting" position STEP 1b. FIG. 6 provides an illustrative conversion chart for calibrating the vODM to adjust for baseline, resting IOP. The measurement of IOP using a tonometer STEP 1b is well known to the art and will not be described in greater detail.

Figure 2:
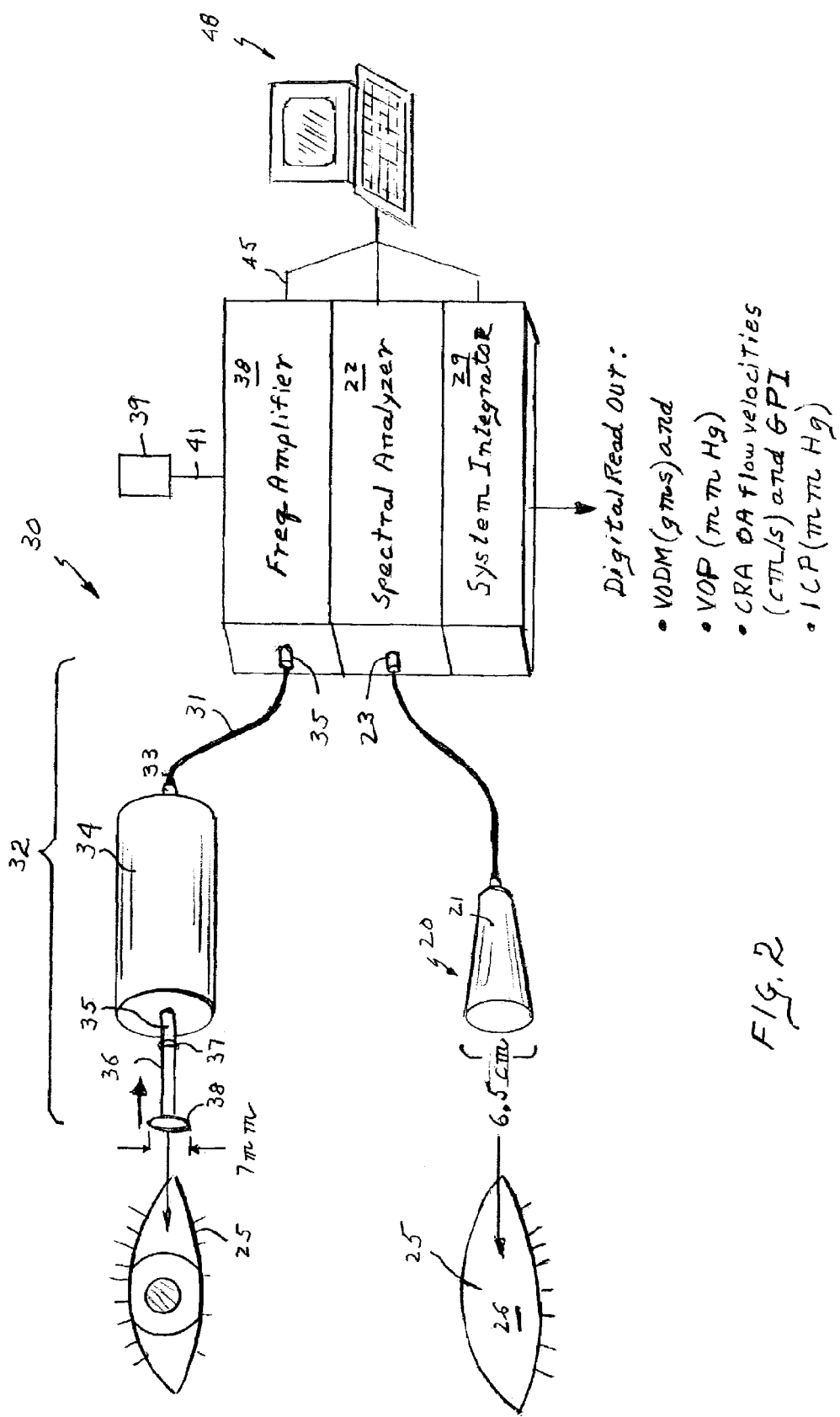
FIG. 2 shows an illustrative embodiment of a system for assessing ICP in accordance with the present invention.

A preferred embodiment of a vODM 30 will now be described. Referring to FIGS. 2 and 3, there are shown, respectively, an illustrative diagrammatic of embodiments of a portable vODM 30 and a displacement transducer 21 therefor. Preferably, the vODM 30 comprises a novel portable ophthalmodynameter that is a significant improvement on the Bailliart device, that is more suitable for measuring intravascular pressure within the lower pressure, venous range, for which the Bailliart device is unsuitable. More preferably, the vODM 30 comprises a differential variable reluctance transducer (DVRT), or displacement transducer 32, e.g., of a type manufactured by MicroStrain® of Burlington, Vt., a frequency amplifier 38, e.g., a 4.8 kHz HBM MVD2555 amplifier of a type manufactured by MicroStrain®, a foot pedal freeze switch 39, and one or more signal cables 31.

In one aspect of the embodied vODM 30, the DVRT 32, having a 1.5 μm resolution, is in communication with the frequency amplifier 38, e.g., via a signal cable 31. One or more cable connections 33 are disposed at a proximal end of the displacement transducer 32. The signal cable 31 can be removably connected to at least one of the one or more cable connections 33 and, further, is removably connectable to an input/output port 35 on the frequency amplifier 38.

The DVRT 32 further comprises a handheld probe portion 34, a movable plunger, or piston, 36, and a convex scleral pressure plate 38. The scleral pressure plate 38 is disposed at a distal end of the DVRT 32, or, more specifically, at the distal end of the plunger 36. The pressure plate 38 has a standardized, convex shape and a standardized surface area. Preferably, the pressure plate 38, e.g., of a type manufactured by Mitutoto Co., can be manufactured with a 6.3 mm diameter and a surface area of 0.33 cm$^2$ using heat resistant metal, ceramic, and like materials. Because the pressure plate 38 physically contacts and applies incremental pressure to the scleral lateral of a patient's orbit 25, the pressure plate 38 should be easily sterilizable and, preferably, autoclavable. More preferably, the scleral pressure plate 38 is removably attachable to the end of the plunger 36, e.g., using a cavity structured and arranged with inner threadings so that corresponding threadings structured and arranged on the outer surface of the plunger 36 can frictionally engage the threadings in the cavity of the pressure plate 38; using outer threadings structured and arranged so that the pressure plate 38 can be removably attached in a cavity (not shown), having corresponding threadings, that is structured and arranged at the distal end of the to the plunger 36; or using an interference fit between the plunger 36 and the pressure plate 38. The removable feature allows users to remove pressure plates 38 after each use for autoclaving to facilitate sanitization.

The probe portion 34 and movable plunger 36 are structured and arranged coaxially so that the moveable plunger 36 can displace freely in an axial direction relative to the handheld probe portion 34. A stop mechanism 37 can be disposed at a discrete location on the shaft of the plunger 36 to prevent excessive stroke, i.e., plunger displacement beyond a desired limitation. In one aspect of the present invention, the stop mechanism 37, e.g., a washer ring, O-ring, and the like, can be slightly larger in outer diameter than the diameter of the opening 35 in the probe 34 through which the plunger 36 travels so that the stroke of the plunger is arrested when the stop mechanism 37 contacts the probe portion 34 at the opening 35. The plunger 36 used by the inventor in his studies was 3.3 cm long with an 8 mm stroke.

A compression spring (not shown) can be structured and arranged in the interior of the probe 34 so as to be in communication with the plunger 36. The compressive spring is structured and arranged in the interior of the probe 34 to enable force measurement for displacement of the plunger 36. An inductive mechanism, e.g., transducer coils, (not shown) also can be structured and arranged in the interior of the probe 34 so that displacement of the moveable plunger 36 induces an electrical signal whereby the greater the displacement, the greater the current and, therefore, the voltage. Thus, axial translation and, therefore, through inductance, signal voltage are a function of applied pressure.

Figure 3A:
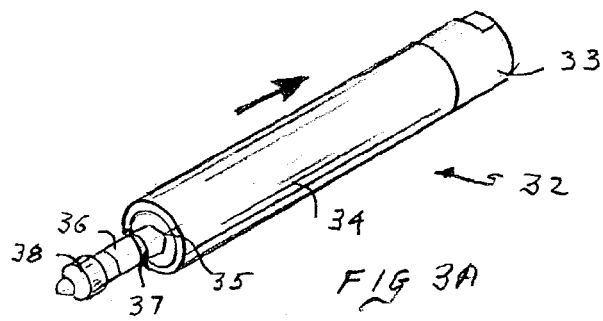
FIG. 3A shows an isometric view of an illustrative embodiment of a vODM displacement transducer for measuring VOP for assessing ICP in accordance with the present invention.
Figure 3B:
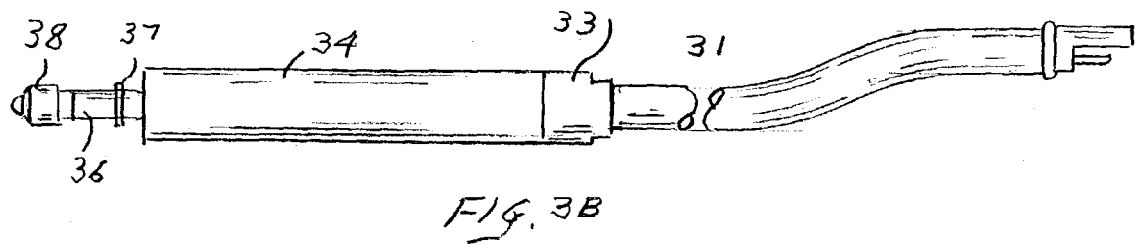
FIG. 3B shows a side view of an illustrative embodiment of a vODM displacement transducer for measuring VOP for assessing ICP in accordance with the present invention.

Preferably, in operation, as the sclera pressure plate 38 is applied incrementally to the lateral sclera of a patient's orbit 25, the plunger 36 displaces axially in the direction shown by the arrow in FIG. 3A. This axial displacement causes the inductive mechanism contained in the probe portion 34 to induce current and therefore produce a voltage, i.e., an output signal, commensurate with the magnitude of the displacement. The output signal, which is measured in real-time, can be transmitted to the frequency amplifier 38 via a signal cable 31, which is in communication with the one or more connections 33 on the DVRT 32. The frequency amplifier 38 includes software and/or hardware or, alternatively, is in communication with such software and/or hardware to convert the analog output signal from the DVRT 32 to digital data, e.g., resultant IOP in mm Hg.

In a preferred embodiment, a foot pedal freeze switch 39, e.g., of a type like the Treadlite II foot pedal, is in communication with the frequency amplifier 38. More preferably, the foot pedal freeze switch 39 communicates with the frequency amplifier 38 via a signal cable 41 that is removably connectable to the frequency amplifier at an I/O port 45 provided for that purpose. The foot pedal freeze switch 39 is in communication with the frequency amplifier 38 for the purpose of transmitting a signal to the frequency amplifier 38 that causes the frequency amplifier 38 to record and store the digital DVRT 32 output signal data at the instant of the signal from the foot pedal 39. In this manner, when a user observes occlusion of a retinal vein, he or she can activate the foot pedal freeze switch 39, which causes the frequency amplifier 38 to record and save the applied pressure in grams and VOP in mm Hg at the instant of occlusion.

Figure 4A:
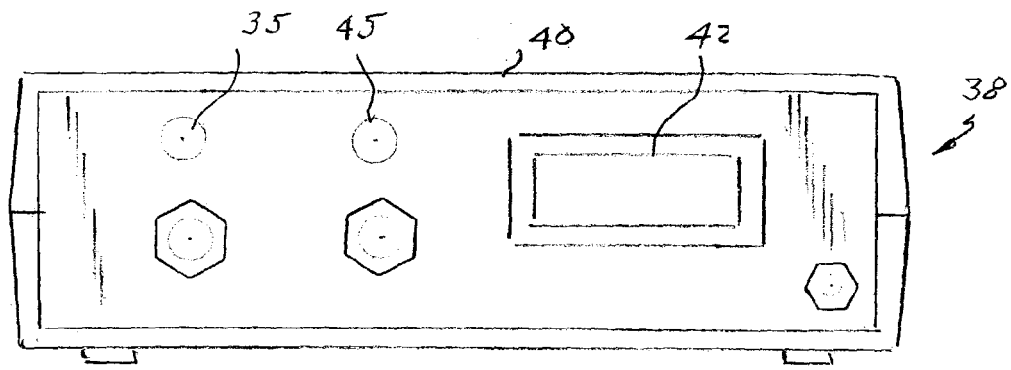
FIG. 4A shows a front elevation view of an illustrative embodiment of a vODM frequency amplifier assessing ICP in accordance with the present invention.
Figure 4B:
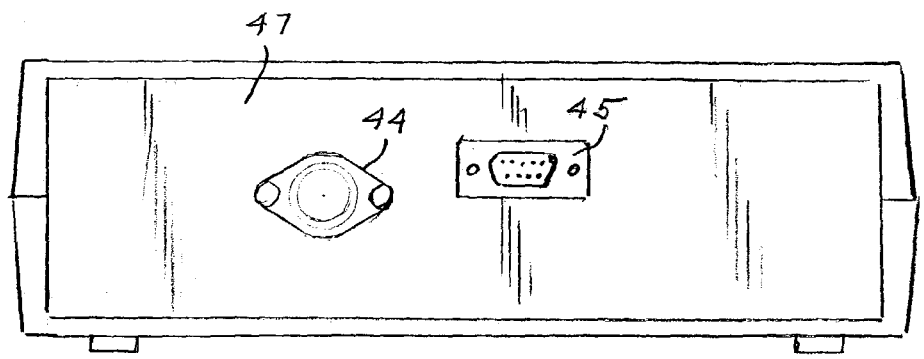
FIG. 4B shows a rear elevation view of an illustrative embodiment of a vODM frequency amplifier assessing ICP in accordance with the present invention.
Figure 5A:
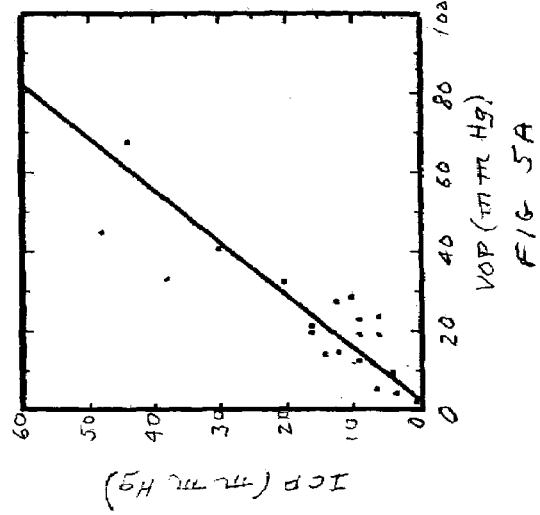
FIG. 5A shows an illustrative plot of the relationship between ICP and VOP.
Figure 5B:
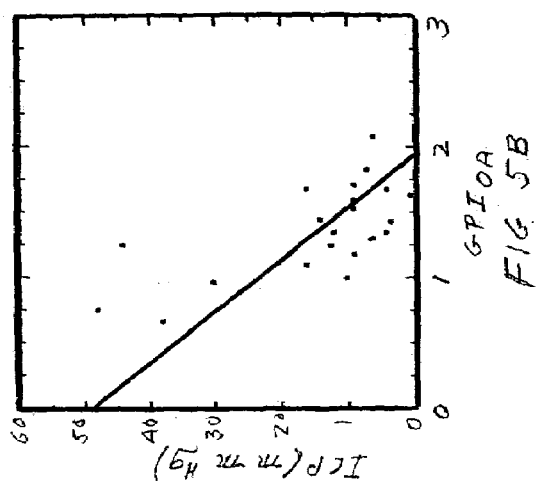
FIG. 5B shows an illustrative plot of the relationship between ICP and GPI of the ophthalmic artery (OA)
Figure 5C:
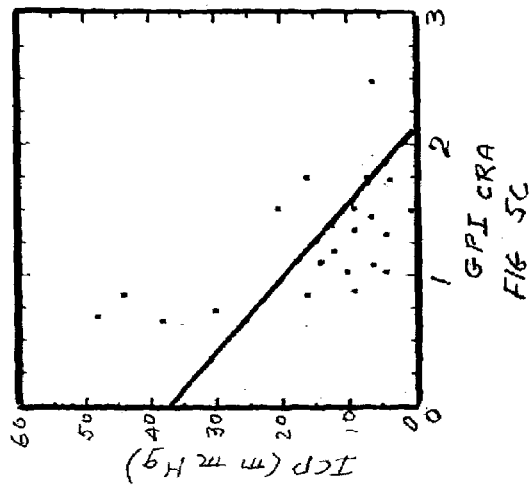
FIG. 5C shows an illustrative plot of the relationship between ICP and GPI of the central retinal artery (CRA)
Figure 5D:
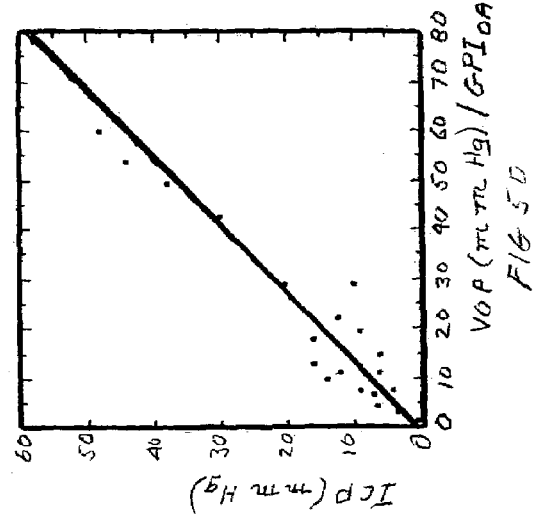
FIG. 5D shows an illustrative plot of the relationship between ICP and VOP/GPI$_{OA}$.
Figure 5E:
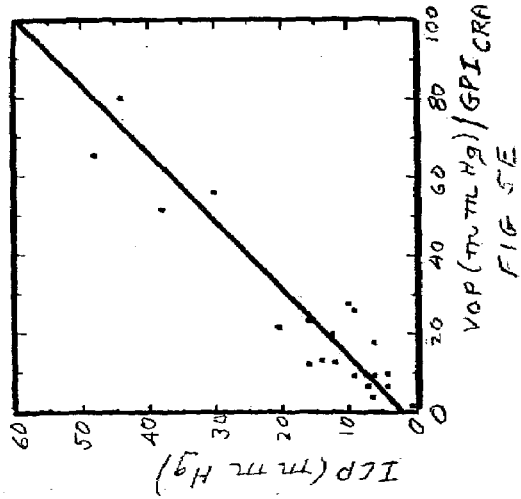
FIG. 5E shows an illustrative plot of the relationship between ICP and VOP/GPI$_{CRV}$.

Referring to FIGS. 4A and 4B, a frequency amplifier 38 will now be described. The purpose of the frequency amplifier 38 is to receive, store, display, modify, and/or transmit load data from the displacement transducer 32. In one embodiment, the frequency amplifier 38 is a two-channel signal conditioning box 40, e.g., an MB-SMT-D smart mother board enclosure manufactured by MicroStrain, Inc. of Burlington, Vt., comprising a modular DEMOD1 circuit card (not shown), 14-bit A/D converter (not shown), and electroluminescent digital display 42, e.g., using a liquid crystal display (LCD), light emitting diode (LED) or the like. Analog data in the form of a voltage signal are transmitted from the displacement transducer 32 to the frequency amplifier 38 via one or more signal cables 31. The real-time position analog signal can then be inverted, i.e., digitized, using the 14-bit A/D converter for display on the digital display 42.

Preferably, the frequency amplifier 38 can store the digital data in internal and/or external memory that is provided for that purpose. More preferably, the frequency amplifier 38 also can transmit digital data, e.g., via an RS-232 I/O port 45, automatically or on demand to a system integrator 29. Such transmission can be direct from the frequency amplifier 38 to the system integrator 29, or, alternatively, via a microprocessor 48, which is in communication with both the frequency amplifier 38 and the system integrator 29. At least one of the microprocessor 48, the frequency amplifier 38, and the system integrator 29 includes a central processing unit, I/O devices, and memory storage means, e.g., random access memory (RAM), read-only memory (ROM), cache memory, and the like, to drive the frequency amplifier 38, the CDI device 22, and the system integrator 29.

The frequency amplifier 38 requires a 12-volt (DC) power source, which can be provided by a transformer (not shown), e.g., a medical grade, isolation transformer, or, more preferably, with replaceable batteries (not shown). A power port 44 can be provided on the back side 47 of the conditioning box 40 if a transformer is used and or, a battery pack (not shown) can be provided in the conditioning box 40 wherein a plurality of batteries, e.g., D cell batteries, can be removably inserted in a manner that is well known to the lesser arts. Preferably, the frequency amplifier 38 includes one or more I/O ports, e.g., an RS-232 port 45, whereby signals and data can be transferred to and from the system integrator 29 and/or a microprocessor 48 that is in communication with both the frequency amplifier 38 and the system integrator 29.

In STEP 4, at least one of the system integrator 29 and/or the microprocessor 48 in communication therewith receives and processes digital data from the frequency amplifier 38 and the CDI device 22 and outputs the data as, e.g., at least one of VOP (in mm Hg), CRA/OA blood flow velocities (in cm/sec), GPI, PRI, and estimated ICP (in mm Hg). The system integrator 29 can include its own internal microprocessor or, alternatively, be in communication with a remote microprocessor.

Having described the methods, systems, and devices of the present invention, we will now provide examples of results using the same. Reference will be made throughout this discussion to FIGS. 5A to 5D and FIG. 6, which provide illustrative examples of representative data from laboratory testing.

The inventor performed non-invasive measurements (n=22) of VOP and transocular arterial blood flow velocity on six patients. The ICP, which was measured invasively by ventriculostomy transducers for comparison purposes, of the patients varied between about 0.5 and about 48 mm Hg. As a starting point, the inventor observed a direct and linear relationship between ICP increase and VOP measured using the vODM described above, which is shown graphically in FIG. 5A. However, no obvious relationships were discernible between ICP and several factors that are known to affect ICP and/or could affect retinal perfusion, e.g., resting IOP, mean systemic arterial pressure (MAP), Hematocrit, $pCO_2$, central venous pressure (CVP), positive end expiratory pressure (PEEP), or temperature.

Some of the variability in venous data was believed to have been derived from localized, arterial-based factors.

However, when arterial effects were analyzed, there was a poor correlation between ICP and mean arterial velocity for both the CRA and OA. Diastolic velocities provided equally bad predictors. However, a significant inverse relationship between the pulsatility amplitude of the CRA, which is defined as the

What is claimed is:

1. A non-invasive system for assessing intracranial pressure, the system comprising:
    a venous outflow pressure (VOP) measuring device to provide venous outflow pressure (VOP) data;
    an ophthalmic or central retinal arterial flow velocity measuring device to provide ophthalmic or central retinal arterial flow velocity data, respectively; and
    a device for determining intracranial pressure (ICP) using venous outflow pressure (VOP) data and a characteristic of the ophthalmic or central retinal artery from ophthalmic or central retinal arterial flow velocity data, respectively.

2. The system as recited in claim 1, wherein the measuring venous outflow pressure (VOP) measuring device comprises a venous ophthalmodynamometer (vODM) in combination with a device for observing collapse of one or more retinal veins in a patient's orbit.

3. The system as recited in claim 2, wherein the device for observing collapse of one or more retinal veins in a patient's orbit is an ophthalmoscope.

4. The system as recited in claim 2, wherein the venous ophthalmodynamometer (vODM) comprises:
    a differential variable reluctance transducer (DVRT) that can be used to apply a recordable, incremental load to a patient's orbit; and
    a frequency analyzer that is in communication with the DVRT for receiving said recordable loading data for recordation.

5. The system as recited in claim 4, wherein the venous ophthalmodynamometer (vODM) further comprises:
    a device for freezing instantaneous load measurements that is in communication with the frequency analyzer, whereby activation of the device will freeze an instantaneous load measurement value at the instant that the retinal vein collapses so that said frozen value can be recorded by the frequency analyzer.

6. The system as recited in claim 1, wherein the system further comprises a device for establishing a baseline, resting intraocular pressure (IOP) so that the baseline, resting intraocular pressure (IOP) can be used to correlate venous outflow pressure (VOP) measurements with intracranial pressure (ICP).

7. The system as recited in claim 6, wherein the device for establishing a baseline, resting intraocular pressure (IOP) is a tonometer.

8. The system as recited in claim 1, wherein the ophthalmic or central retinal arterial flow velocity measuring device comprises a color Doppler imagining (CDI) device, wherein the CDI device further comprises a Doppler probe and a spectral analyzer;
    wherein the Doppler probe can be applied to at least one of a patient's closed eyelids and a first ultrasound signal from said Doppler probe can provide an orbital scan image of said at least one of a patient's orbits to identify an optic nerve head of said orbit and a second ultrasound signal from said Doppler probe can provide a visual image of anterograde arterial blood flow in at least one artery of the patient's orbit to identify a vessel region to measure arterial blood flow velocity; and a third ultrasonic signal from said Doppler probe can provide continuous arterial blood flow velocity data at the identified vessel region.

9. The system as recited in claim 8, wherein the spectral analyzer comprises:
    a display device for displaying the orbital scan image in two dimensions;
    an input/output device for identifying the vessel region in said orbital scan image using the second ultrasound signal.

10. The system as recited in claim 1, wherein the device for determining a characteristic of the ophthalmic or central retinal artery comprises at least one of a system integration device and a microprocessor in combination with a system integration device.

11. The system as recited in claim 10, wherein the said at least one of a system integration device and a microprocessor in combination with a system integration device can calculate at least one of peak systolic velocity (PSV), end diastolic velocity (EDV), and mean arterial velocity (MAV) from measured ophthalmic or central retinal arterial blood flow velocity data.

12. The system as recited in claim 11, wherein said at least one of a system integration device and a microprocessor in combination with a system integration device can further calculate Gosling's pulsatility index (GPI) in accordance with the following mathematical formula:

$$GPI=(PSV-EDV)/MAV.$$

13. The system as recited in claim 12, wherein the device for determining intracranial pressure (ICP) using a relationship between venous outflow pressure (VOP) data and a pulsatility characteristic of the ophthalmic or central retinal artery includes means for calculating ICP using the following mathematical formula:

$$ICP=VOP/GPI.$$

14. The system as recited in claim 11, wherein said at least one of a system integration device and a microprocessor in combination with a system integration device can further calculate Pourcelot's resistive index (PRI) in accordance with the following mathematical formula:

$$PRI=(PSV-EDV)/PSV.$$

15. The system as recited in claim 14, wherein the device for determining intracranial pressure (ICP) using a relationship between venous outflow pressure (VOP) data and a resistivity characteristic of the ophthalmic artery includes means for calculating ICP using the following mathematical formula:

$$ICP=VOP/PRI.$$

16. The system as recited in claim 1, wherein the intracranial pressure assessed is at least one of an absolute intracranial pressure and a change in intracranial pressure.

17. The system as recited in claim 1, wherein the intracranial pressure assessed is at least one of an absolute intracranial pressure and a change in intracranial pressure.

18. The system as recited in claim 1, wherein the venous outflow pressure (VOP) measuring device system comprises:
    a displacement transducer for applying pressure to a lateral sclera of the patient's orbit incrementally, the transducer further comprising:
    a probe portion that includes a compression spring and an induction mechanism, a plunger that is structured and arranged coaxial to to probe portion, wherein at least some portion of the plunger is disposed inside the probe portion and is, further, in communication with the compression spring, and a removable pressure plate for applying incremental pressure to the patient's lateral sclera that is structured and arranged at a distal end of the plunger transducer, wherein as pressure is applied to the lateral sclera of the patient's orbit, the plunger displaces so as to compress the compression spring in the probe portion, which induces a current commensurate with the magnitude of displacement in the induction mechanism; and a frequency analyzer that is in communication with the displacement transducer, wherein current induced by displacement of the plunger is output to the frequency analyzer as an output signal, which output signal can be processed by said frequency analyzer to provide venous occlusion pressure (VOP) data.

19. The system as recited in claim 18, wherein the device further comprises a foot pedal that is in communication with the frequency analyzer, wherein, when activated, the foot pedal transmits a signal to said frequency analyzer causing said frequency analyzer to freeze, record, and store the instantaneous venous occlusion pressure (VOP) data.

20. The system as recited in claim 18, wherein the frequency analyzer is in communication with at least one of an internal or an external microprocessor, the internal or external microprocessor comprising a central processing unit, one or more input/output devices, and at least one of random access memory, read-only memory, and cache memory.

* * * * *